US012721701B2

(12) United States Patent
Hunter et al.

(10) Patent No.: US 12,721,701 B2
(45) Date of Patent: Sep. 1, 2026

(54) OSTEOCONDUCTIVE CERAMIC COMPOSITE BIOMATERIAL UTILIZING SOLUTION-POLYMERIZED ACRYLIC CARRIER AND METHOD OF MANUFACTURE

(71) Applicant: Orthomod LLC, Dayton, OH (US)

(72) Inventors: Shawn A. Hunter, Springboro, OH (US); David Louis Kirschman, Dayton, OH (US); Dewey J. Weeda, Beavercreek, OH (US)

(73) Assignee: Orthomod LLC, Dayton, OH (US)

( * ) Notice: Subject to any disclaimer, the term of this patent is extended or adjusted under 35 U.S.C. 154(b) by 215 days.

(21) Appl. No.: 18/791,931

(22) Filed: Aug. 1, 2024

(65) Prior Publication Data

US 2025/0041027 A1 Feb. 6, 2025

Related U.S. Application Data

(60) Provisional application No. 63/517,032, filed on Aug. 1, 2023.

(51) Int. Cl.
*A61C 8/02* (2006.01)
*A61C 8/00* (2006.01)
*A61K 6/802* (2020.01)
*A61K 6/887* (2020.01)

(52) U.S. Cl.
CPC .......... *A61C 8/0006* (2013.01); *A61C 8/0016* (2013.01); *A61K 6/802* (2020.01); *A61K 6/887* (2020.01)

(58) Field of Classification Search
CPC .... A61C 8/0006; A61C 8/0016; A61K 6/887; A61K 6/802
See application file for complete search history.

(56) References Cited

U.S. PATENT DOCUMENTS

2015/0202052 A1 7/2015 Dimauro
2019/0117281 A1 4/2019 Stein
2020/0268929 A1* 8/2020 Suh .......................... A61L 24/02
2021/0022867 A1* 1/2021 Shimko .................. B33Y 70/00
2022/0296780 A1* 9/2022 Kirschman ............. A61L 27/46
2022/0395373 A1 12/2022 Shimko
2023/0321317 A1 10/2023 Suh

FOREIGN PATENT DOCUMENTS

WO WO-2011051731 A2 * 5/2011 ............. A61L 27/26

OTHER PUBLICATIONS

International Search Report dated Dec. 5, 2024 pertaining to PCT/US2024/040539 filed Aug. 1, 2024.

* cited by examiner

*Primary Examiner* — Sean M Basquill
(74) *Attorney, Agent, or Firm* — Dinsmore & Shohl LLP

(57) ABSTRACT

Provided herein are surgical implants and methods of manufacturing the implants. The implants are generally osteoconductive composite implants utilizing minimally-crosslinked acrylic carriers combined with osteoconductive ceramics. The methods generally involve dissolving a monomer and an initiator in a solvent to form a reaction mixture, controlling the temperature and viscosity of the reaction mixture to allow solution polymerization, polymerizing the monomer in the reaction mixture to form an acrylic carrier, recovering the acrylic carrier, extruding the acrylic carrier with an osteoconductive ceramic to form an osteoconductive biomaterial, and processing the osteoconductive biomaterial to form the osteoconductive composite implant.

20 Claims, 5 Drawing Sheets

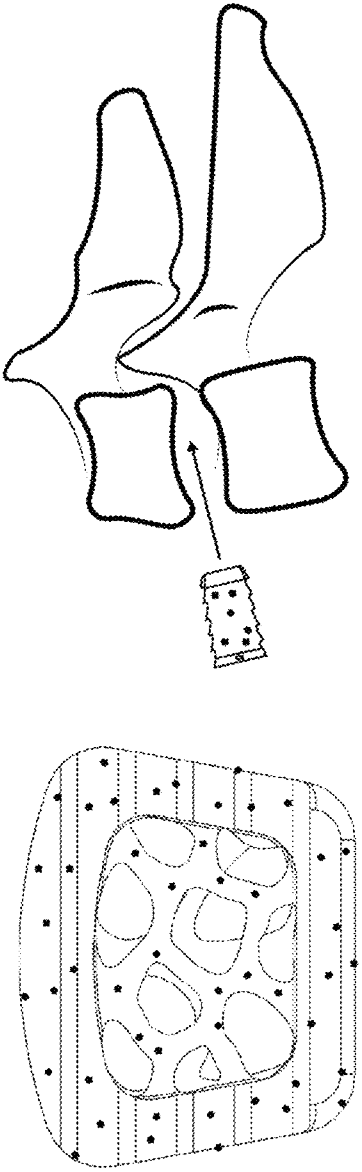
FIG. 5: Final Implant Structure Images showing the final implant structure, in this embodiment a cervical spine intervertebral implant with lateral view to display the dispersion of ceramic within the polymer matrix.

OSTEOCONDUCTIVE CERAMIC COMPOSITE BIOMATERIAL UTILIZING SOLUTION-POLYMERIZED ACRYLIC CARRIER AND METHOD OF MANUFACTURE

CROSS-REFERENCES TO RELATED APPLICATIONS

This application is a continuation of United States Patent Application, which claims benefit of priority to U.S. Provisional Application No. 63/517,032, filed Aug. 1, 2023.

TECHNICAL FIELD

The present disclosure relates generally to the field of orthopedic biomaterials, more specifically, to compositions utilizing solution-polymerized acrylic to achieve a biocompatible thermoplastic carrier for osteoconductive ceramics.

BACKGROUND

Polymerized acrylics such as poly methyl methacrylate (PMMA) are often used in surgical procedures as bone cements and short-term implants. These acrylics are highly-crosslinked, resulting from a bulk polymerization process via chemical reaction wherein the acrylic monomer is directly polymerized without the use of a solvent or diluent. An example of this would be mixing methyl methacrylate (MMA, the monomer for PMMA) with an initiator like benzoyl peroxide. The reaction starts with the initiation step, followed by propagation and eventually termination. This results in a polymer product which is highly-crosslinked, hard and brittle. Bulk-polymerized, highly crosslinked acrylic has poor fatigue and crack resistance and is not generally appropriate for the manufacture of long-term load-bearing surgical implants.

Alternatively, acrylics can be manufactured using a solution polymerization rather than bulk polymerization. In this method, both the monomer and the initiator are dissolved in a solvent such as absolute ethanol before polymerization. The solvent helps control the temperature and viscosity of the reaction mixture, allowing for better control over the reaction. The resulting polymer chains are significantly more linear and less crosslinked than bulk-polymerized acrylics.

Acrylic polymers are not osteoactive, and must be used along with bone grafts or synthetic orthobiologics in order to stimulate bone healing. The controlled addition of osteoconductive ceramics to acrylic polymers could be beneficial, however the undesirable chemical and physical properties of highly crosslinked, bulk-polymerized acrylics limit the utility of such a process.

Accordingly, a need exists for high-strength, fatigue-resistant implants with osteoconductive properties and manufacturing methods that effectively incorporate osteoactive granules, while ensuring mechanical robustness to enhance osteoconduction and overall implant performance.

SUMMARY

This present disclosure relates to compositions comprising polymerized acrylic, osteoconductive ceramic implants, and biomaterials, including the compositions, and methods of manufacture and use of the same.

In one embodiments, the present disclosure relates to a method for producing an osteoconductive composite implant. The method generally involves dissolving a monomer and an initiator in a solvent to form a reaction mixture, controlling the temperature and viscosity of the reaction mixture to allow solution polymerization, polymerizing the monomer in the reaction mixture to form an acrylic carrier, recovering the acrylic carrier, extruding the acrylic carrier with an osteoconductive ceramic to form an osteoconductive biomaterial, and processing the osteoconductive biomaterial to form the osteoconductive composite implant.

In another embodiments, the present disclosure relates to a method for producing an osteoconductive ceramic biomaterial using a substantially non-crosslinked, linear, or branched acrylic carrier. In some embodiments, the method involves dissolving a monomer and an initiator in a solvent to form a reaction mixture. Optionally, the acrylic carrier is produced through one of three polymerization processes: bulk polymerization with controlled crosslinking, suspension polymerization, or emulsion polymerization. In some embodiments, such as in bulk polymerization with controlled crosslinking, the acrylic carrier produced has minimal crosslinking, retaining its thermoplastic properties. In some embodiments, such as in suspension polymerization, the monomer is polymerized in a continuous aqueous phase, forming discrete polymer particles. In some embodiments, such as in emulsion polymerization, the monomer molecules polymerize within formed micelles.

Additional features and advantages of the embodiments described herein will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 5 illustrates a cross-sectional view of a cervical spine intervertebral implant, according to one or more embodiments described herein.

DETAILED DESCRIPTION

Figure 1:
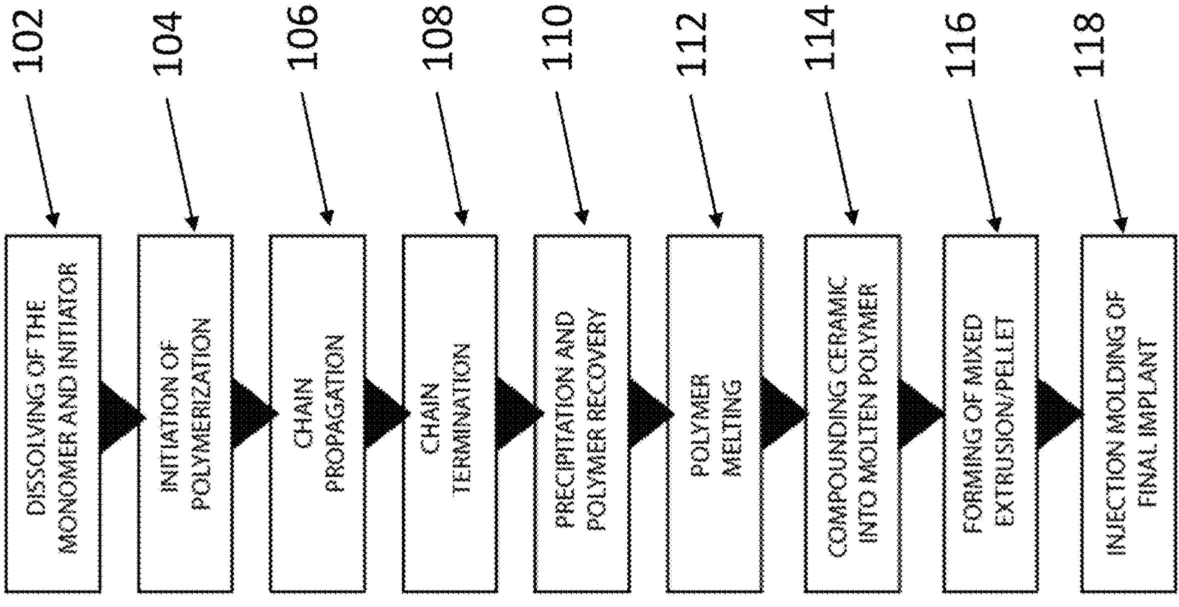
FIG. 1 illustrates a flowchart, depicting a method of producing an osteoconductive biomaterial according to one or more embodiments described herein.
Figure 1:

The above described deficiencies are addressed by the present disclosure, which combines minimally-crosslinked acrylics with osteoconductive ceramics to create implants having high-strength, fatigue-resistant implants with osteoconductive properties.

Embodiments of the present disclosure generally relate to surgical implants and methods of manufacture. In some embodiments, the present disclosure relates to a method for producing an osteoconductive composite implant. The method generally involves dissolving a monomer and an initiator in a solvent to form a reaction mixture, controlling the temperature and viscosity of the reaction mixture to allow solution polymerization, polymerizing the monomer in the reaction mixture to form an acrylic carrier, recovering the acrylic carrier, extruding the acrylic carrier with an osteoconductive ceramic to form an osteoconductive biomaterial, and processing the osteoconductive biomaterial to form the osteoconductive composite implant.

As noted above, conventional osteoconductive ceramics typically employ traditional bulk polymerized acrylics that are highly cross-linked. These standard materials have limitations in certain performance aspects. In contrast, the embodiments described in the present disclosure introduce an innovative approach by integrating minimally-crosslinked acrylics with osteoconductive ceramics. This combination results in implants that exhibit superior mechanical properties, including high strength and fatigue resistance. Specifically, the use of minimally-crosslinked acrylics enhances several key performance metrics compared to conventional devices, including interfacial bonding, stress distribution, processing flexibility, and ceramic loading.

The disclosure should not be construed as limited to the embodiments set forth herein. Rather, these embodiments are provided so that this disclosure will be thorough and complete, and will fully convey the subject matter to those skilled in the art.

Unless otherwise defined, all technical and scientific terms used herein have the same meaning as commonly understood by one of ordinary skill in the art. The terminology used in the disclosure herein is for describing particular embodiments only and is not intended to be limiting.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used in the specification and the appended claims, the singular forms "a," "an," and "the" are intended to include the plural forms as well, unless the context clearly indicates otherwise. Thus, for example, reference to "a" component includes aspects having two or more such components, unless the context clearly indicates otherwise.

As used herein "osteoconductive" and grammatical equivalents thereof refers to the ability of a material to serve as a scaffold or matrix that supports the growth and attachment of new bone cells. An osteoconductive material facilitates the migration, attachment, and proliferation of osteoblasts on its surface, promoting the formation of new bone tissue. For example and without being bound by theory, osteoconductive materials may create a conducive environment for bone regeneration by providing physical and chemical cues to support cellular activities related to bone formation.

The present disclosure generally relates to methods for producing an osteoconductive composite implant, described in greater detail herein. In some embodiments, the methods disclosed herein employ solution polymerization to form a polymerized acrylic carrier. Generally, the methods include dissolving a monomer and an initiator in a solvent to form a reaction mixture; controlling the temperature and viscosity of the reaction mixture; polymerizing the monomer; recovering the solution-polymerized acrylic carrier; extruding the acrylic carrier with an osteoconductive ceramic to form an osteoconductive biomaterial; and processing the osteoconductive biomaterial to form the osteoconductive composite implant.

Turning now to FIG. 1, a flow chart illustrating an exemplary method 100 of producing osteoconductive ceramic biomaterials and/or implants is depicted. In embodiments, the production of osteoconductive ceramic composite biomaterials and/or implants involves a series of controlled steps to achieve a biocompatible, thermoplastic carrier for osteoconductive ceramics. The process generally includes the polymerization of an acrylic carrier followed by the extrusion of the acrylic carrier with an osteoconductive ceramic. Various polymerization techniques may be employed, including solution polymerization, bulk polymerization with controlled crosslinking, suspension polymerization, and emulsion polymerization. In some embodiments, the polymerization technique is solution polymerization.

In some embodiments, such as depicted at block 102, the solution polymerization involves dissolving a monomer and an initiator in a solvent to form a reaction mixture. As will be readily apparent to a person of skill in the art, the individual components of the reaction mixture can be selected for intended polymerization rate, molecular weight, molecular weight distribution, polymerization temperature, strength, thermal stability, flexibility, and the like.

Any suitable solvent may be used in the dissolution of the monomer and initiator at block 102. Suitable solvents include, but are not limited to ethanol, methanol, isopropanol, acetone, dimethyl sulfoxide, ethyl acetate, and acetonitrile. In some embodiments, the solvent is absolute ethanol. It will be appreciated that different solvents may influence the polymerization process in various ways. For example, and without being bound by theory, ethanol is a polar solvent that may be used to effectively dissolve monomers and/or initiators, thereby providing a stable reaction environment.

Absolute ethanol offers the opportunity to create a water-free reaction mixture. Further, the relatively low boiling point allows for casy removal after polymerization, facilitating the recovery of the solution-polymerized acrylic. Further, methanol, another polar solvent, offers similar properties to ethanol, but with slightly different solubility characteristics and reaction rates. Isopropanol, acetone, dimethyl sulfoxide, ethyl acetate, and acetonitrile each have unique properties that may be leveraged to optimize the polymerization process. For example, acetone, a highly volatile solvent, may facilitate rapid solvent removal after polymerization, while dimethyl sulfoxide, with its high boiling point, enables higher reaction temperatures.

It will be appreciated that the choice of solvent may impact the dissolution of the monomer and/or initiator, facilitate homogenization before polymerization, and/or provide a medium for reaction and/or polymerization. For example and without being bound by theory, the solvent may act as a vehicle to dissolve the monomer and initiator, ensuring a uniform reaction mixture. It will be appreciated that a uniform reaction mixture may lead to a more consistent polymer.

Furthermore, the solvent may provide a controlled reaction environment. For example, and without being bound by theory, the solvent may help regulate the temperature of the reaction mixture, preventing localized overheating, which may lead to side reactions and/or degradation of the polymer. By moderating the reaction temperature, the solvent may lead to the formation of a steady and uniform polymerization rate, resulting in polymers with more consistent molecular weights and properties. Additionally, the solvent may control the viscosity of the reaction mixture. Without being bound by theory, controlling the viscosity may aid in maintaining adequate mixing and/or preventing the reaction mixture from becoming too viscous, which may hinder the polymerization process, potentially leading to incomplete reactions or irregular polymer chains.

In some embodiments, the solvent may provide a medium for the initiator to generate free radicals, described in greater detail herein. It will be appreciated that, in a solvent-based system, the free radicals may diffuse more freely, increasing their chances of encountering and reacting with monomer molecules. This diffusion enhances the efficiency of the polymerization process and may contribute to the formation of high-quality polymers.

As noted briefly above, the solvent is used to dissolve the monomer and initiator to form the reaction mixture. It will be appreciated that different monomers may be chosen for desired properties of the polymer, the polymerization method, the chemical compatibility with the solvent and/or initiator, and/or the end-use application of the polymer. The monomer may be any suitable molecule that can undergo polymerization, including acrylate and methacrylate monomers, vinyl monomers, diene monomers, condensation monomer, and functional monomers. Illustrative, non-limiting methacrylate monomers include methyl methacrylate, ethyl methacrylate, butyl methacrylate. Additional monomers include, but are not limited to, ethylene, vinyl chloride, styrene, acrylonitrile, acrylic acid, and combinations thereof. In some embodiments, the monomer is a methacrylate monomer. In some embodiments, the monomer is methyl methacrylate.

The reaction mixture also includes an initiator. Generally, the initiator decomposes to produce reactive species (such as free radicals or ions) that initiate the polymerization of monomers, leading to the formation of polymer chains.

The initiator may be any molecule that initiates or starts the polymerization reaction. In some embodiments, the initiator undergoes a chemical reaction that initiates the polymerization of the monomer. For example, in some embodiments, an initiator is induced by an energy source (e.g. heat, light, ultrasonic energy, etc.) to release free radicals. The free radicals may facilitate the formation of covalent bonds between molecules of the monomer, allowing them to form polymer chains. Any initiator capable of triggering polymerization may be used. Illustrative, non-limiting examples of initiators include azobisisobutyronitrile, benzoyl peroxide, 2,2'-azobis(2-methylpropionamidine) dihydrochloride (V-50), 2,2'-Azobis[2-(2-imidazolin-2-yl)propane] dihydrochloride (VA-044), 2,2'-azobis(2-amidinopropane) dihydrochloride (V-511), di-tert-butyl peroxide (DTBP), cumene hydroperoxide, potassium sulfate, and/or combinations thereof. In some embodiments, the initiator is azobisisobutyronitrile.

It will be appreciated that the selection of the specific initiator may be to influence the rate of polymerization, the polymerization temperature, the molecular weight distribution of the polymer, and/or the overall properties of the final product. It will be further appreciated that the choice of initiator and its decomposition rate may influence the polymer's microstructure, including branching, cross-linking, and stereochemistry. For example, and without being bound by theory using a peroxide initiator may lead to a higher degree of cross-linking, resulting in a more rigid polymer network. The initiator may control the polymerization rate by the decomposition rate of the initiator. The decomposition rate of the initiator affects the rate at which reactive species are generated. Faster decomposition leads to a higher concentration of reactive species, increasing the polymerization rate, while slower decomposition results in a lower concentration of reactive species, slowing down the polymerization process.

The concentration of initiator may also influence the molecular weight of the resulting polymer. A higher initiator concentration leads to more reactive species, resulting in shorter polymer chains and lower molecular weight polymers, while lower initiator concentrations produce fewer reactive species, allowing the formation of longer polymer chains and higher molecular weight polymers. The thermal stability and mechanical strength of the polymer may also be affected by the choice of initiator. Initiators that promote uniform polymerization tend to produce polymers with better mechanical properties, while initiators that decompose at lower temperatures may be used to control the thermal properties of the polymer, making them suitable for applications requiring specific thermal characteristics.

In some embodiments, the reaction mixture also includes a cross-linking copolymer. In some embodiments, the cross-linking copolymer to create a 3-dimensional network structure. Optionally, the crosslinking copolymer cross-links one or more polymer chains to another polymer chain. It will be appreciated that the crosslinking copolymer may be selected to impact the mechanical strength, thermal resistance, and/or stability of the osteoconductive biomaterials and/or osteoconductive composite implants, described in greater detail herein. In some embodiments, the crosslinking copolymer is allyl methacrylate. As an example, and without being bound by theory, in some embodiments, allyl methacrylate may react to form covalent bonds with methyl methacrylate and with other allyl methacrylate molecules to form 3-dimensional structures.

In some embodiments, producing an osteoconductive composite implant includes polymerizing the monomer in the reaction mixture to form an acrylic carrier. In some embodiments, polymerizing the monomer involves initiating polymerization, chain propagation and/or chain termination, described in greater detail herein.

Still referring to FIG. 1, after the monomer and the initiator are dissolved in the solvent, in some embodiments, the method 100 includes the initiation of polymerization, depicted at block 104. Generally, initiation of polymerization involves the generation of active species, such as free radicals, cations, or anions, depending on the type of polymerization. These active species react with monomers to initiate the polymer chain, described in greater detail herein.

In free radical polymerization, initiators, such as azobisisobutyronitrile, benzoyl peroxide, cumene hydroperoxide, and the like, decompose under heat or light to produce frec radicals. For example, and without being bound by theory, in some embodiments, azobisisobutyronitrile may thermally decompose to yield two free radicals, which then react with monomers such as methyl methacrylate, initiating the polymer chain. In cationic polymerization, initiators such as Lewis acids or protonic acids generate cations that react with monomers, such as styrene, which contain electron-rich double bonds. In anionic polymerization, initiators like alkali metals or strong bases produce anions that react with monomers featuring electrophilic sites, such as butadiene.

It will be appreciated that initiation may be influenced by various factors, including temperature, which may affect the rate of initiator decomposition and radical generation; the concentration of the initiator, which may impact the number of radicals produced; and/or light exposure for photoinitiators. Additionally, as described in greater detail herein, the choice of solvent may affect the solubility of initiators and/or monomers, thereby influencing the initiation rate and efficiency. It will be appreciated that tailoring the properties of the resulting polymers may be influenced by adjusting one or more of these parameters.

In some embodiments, the method 100 includes propagation of the polymer, depicted at block 106. Propagation of the polymer, also referred to as chain propagation is a central phase in the polymerization process 100 where active polymer chains extend through the sequential addition of monomer units. Once the polymerization is initiated, the active site on the growing polymer chain, often a free radical, cation, or anion, reacts with the double bond of a monomer molecule. This reaction results in the formation of a new covalent bond between the monomer and the polymer chain, thereby extending the chain length. During chain propagation, the active site on the growing polymer chain remains reactive, allowing it to continue reacting with additional monomer molecules.

It will be appreciated that the rate of propagation may be influenced by several factors, including the concentration of monomers, the reactivity of the monomers, and the temperature of the reaction. In free radical polymerization, for example, the active center is a free radical that reacts with the monomer's double bond, creating a new radical at the end of the growing chain. This new radical then reacts with another monomer, continuing the process. The efficiency of propagation can be affected by the stability of the radicals and the availability of monomers. Similarly, in cationic and anionic polymerizations, the active center is a cation or anion that facilitates the addition of monomers to the growing chain through nucleophilic or electrophilic mechanisms.

In some embodiments, chain propagation continues until the monomer supply is exhausted or until the polymer chain is terminated, as depicted in block 108, described in greater detail herein. It will be appreciated that controlling factors such as monomer concentration, reaction temperature, and initiator concentration, impacts chain propagation, thereby determining the molecular weight and overall properties of the polymer.

In some embodiments, producing an osteoconductive composite implant includes controlling the temperature and/or viscosity of the reaction mixture to allow solution polymerization. In some embodiments, the reaction mixture is maintained at a specific temperature or within a range of temperatures. In some embodiments, the reaction mixture is maintained with a specific viscosity or within a range of viscosity to facilitate polymerization in the solution. In some embodiments, the reaction mixture is maintained at a specific temperature or within a range of temperatures and with a specific viscosity or within a range of viscosity to facilitate polymerization in the solution.

It will be appreciated that the temperature of the reaction mixture may impact the polymerization process and the end characteristics of the polymer. For example, and without being bound by theory, at higher temperatures, the increased rate of initiation and propagation may lead to more polymer chains being formed. However, the increased termination rates can reduce the molecular weight by terminating chains more quickly. Further, the temperature may also affect the structural properties of the resulting polymer. For instance, at higher temperatures, the increased mobility of the growing polymer chains may lead to different microstructures, such as tacticity (the arrangement of substituent groups along the polymer chain) and branching.

Temperatures and/or temperature ranges of polymerization reactions generally allow the reaction to proceed without thermal degradation and/or side reactions. In some embodiments, the temperature range is between 50° C.-100° C. However, the temperature range may be adjusted based on the type of polymerization, the initiator, the polymerization rate, and/or the intended application of the resultant polymer. In some embodiments, the reaction mixture is maintained at a specific temperature or within a range of temperatures to facilitate polymerization in the solution.

For example, and without being bound by theory, in some embodiments, when bulk polymerization is used, the temperature may be maintained from about 50° C. to about 85° C., including about 50° C., about 55° C., about 60° C., about 65° C., about 70° C., about 75° C., about 80° C., and about 85° C., including any range having any endpoint defined by any two of the aforementioned values. In some embodiments, the temperature may be maintained from about 60° C. to about 80° C.

In some embodiments, for example when solution polymerization is used, the temperature may be maintained from about 45° C. to about 70° C., including about 45° C., about 50° C., about 55° C., about 60° C., about 65° C., and about 70° C., including any range having any endpoint defined by any two of the aforementioned values. In some embodiments, the temperature may be maintained from about 50° C. to about 70° C.

In some embodiments, for example when suspension polymerization is used, the temperature may be maintained from about 60° C. to about 100° C., including about 60° C., about 65° C., about 70° C., about 75° C., about 80° C., about 85° C., about 90° C., about 95° C., and about 100° C. including any range having any endpoint defined by any two of the aforementioned values. In some embodiments, the temperature may be maintained from about 60° C. to about 90° C.

It will be appreciated that the viscosity of the reaction mixture may impact the polymerization process, such as the diffusion rates of reactants, heat transfer, and reaction kinetics, thereby impacting the end characteristics of the polymer. In some embodiments, the viscosity of the reaction medium may affect the kinetic parameters of polymerization. For example, and without being bound by theory, in highly viscous systems, the rate constants for both propagation and termination reactions may be altered. For example, in free radical polymerization, the reduced mobility of radicals in a viscous medium may lower the termination rate constant, leading to higher polymerization degrees.

In some embodiments, the viscosity may be adjusted during polymerization. Lower viscosities make mixing and homogenization easier, while higher viscosities can slow the reaction rate. In some embodiments, the viscosity of the reaction mixture may be influenced by the choice of solvent. In some embodiments, the reaction mixture is maintained with a specific viscosity or within a range of viscosity to facilitate polymerization in the solution. In some embodiments, the viscosity may be from about 0.01 Pa·s to about 15 Pa·s.

For example, and without being bound by theory, in some embodiments, when bulk polymerization is used, the viscosity may be maintained from about 0.1 Pa·s to about 15 Pa·s, including about 0.1 Pa·s, about 0.5 Pa·s, about 1.0 Pa·s, about 1.5 Pa·s, about 2.0 Pa·s, about 2.5 Pa·s, about 3.0 Pa·s, about 3.5 Pa·s, about 4.0 Pa·s, about 4.5 Pa·s, about 5.0 Pa·s, about 5.5 Pa·s, about 6.0 Pa·s, about 6.5 Pa·s, about 7.0 Pa·s, about 7.5 Pa·s, about 8.0 Pa·s, about 8.5 Pa·s, about 9.0 Pa·s, about 9.5 Pa·s, about 10.0 Pa·s, about 10.5 Pa·s, about 11 Pa·s, about 12 Pa·s, about 13 Pa·s, about 14 Pa·s and about 15 Pa·s, including any range having any endpoint defined by any two of the aforementioned values. In some embodiments, the viscosity may be maintained from about 0.1 Pa·s to about 10 Pa·s.

In some embodiments, for example when solution polymerization is used, the viscosity may be maintained from about 0.01 Pa·s to about 1.5 Pa·s, including about 0.01 Pa·s, about 0.05 Pa·s, about 0.1 Pa·s, about 0.15 Pa·s, about 0.20 Pa·s, about 0.25 Pa·s, about 0.3 Pa·s, about 0.35 Pa·s, about 0.4 Pa·s, about 0.45 Pa·s, about 0.5 Pa·s, about 0.55 Pa·s, about 0.6 Pa·s, about 0.65 Pa·s, about 0.7 Pa·s, about 0.75 Pa·s, about 0.8 Pa·s, about 0.85 Pa·s, about 0.9 Pa·s, about 0.95 Pa·s, about 1.0 Pa·s, about 1.1 Pa·s about 1.2 Pa·s, about 1.3 Pa·s, about 1.4 Pa·s, and about 1.5 Pa·s, including any range having any endpoint defined by any two of the aforementioned values. In some embodiments, the viscosity may be maintained from about 0.01 Pa·s to about 1.0 Pa·s.

In some embodiments, for example when suspension polymerization is used, the viscosity may be maintained from about 0.1 Pa·s to about 7.5 Pa·s, including about 0.1 Pa·s, about 0.5 Pa·s, about 1.0 Pa·s, about 1.5 Pa·s, about 2.0 Pa·s, about 2.5 Pa·s, about 3.0 Pa·s, about 3.5 Pa·s, about 4.0 Pa·s, about 4.5 Pa·s, about 5.0 Pa·s, about 5.5 Pa·s, about 6.0 Pa·s, about 6.5 Pa·s, about 7.0 Pa·s, and about 7.5 Pa·s, including any range having any endpoint defined by any two of the aforementioned values. In some embodiments, the viscosity may be maintained from about 0.01 Pa·s to about 5.0 Pa·s.

In some embodiments, the polymerization method 100 includes a chain termination step, depicted in block 108. In chain termination, the active growth of polymer chains is halted, leading to the formation of the final polymer product. This phase of the polymerization process generally involve the cessation of chain elongation, resulting in the stabilization of the polymer chains at a particular length. It will be appreciated that the termination mechanism may vary depending on the type of polymerization process used.

For example, in radical polymerization, chain termination generally occurs through two primary mechanisms: combination and disproportionation. In the combination mechanism, two active polymer radicals react with each other to form a single, stable polymer chain. This reaction effectively ends the growth of both chains as the radical centers are neutralized, leading to the formation of a longer polymer chain without any active sites remaining. In the disproportionation mechanism, a radical chain ends by transferring a hydrogen atom from one polymer radical to another, resulting in the formation of two stable polymer chains with a terminal double bond and a saturated end group. Both mechanisms lead to the cessation of the polymerization process for the involved chains. In some embodiments, the termination mechanism is controlled through the polymerization conditions. For example, and without being bound by theory, in some embodiments, higher temperatures increase the rate of termination reactions, affecting the molecular weight and polymerization efficiency.

The efficiency and type of termination mechanism may influence the molecular weight, distribution, and overall properties of the final polymer. For example, a combination termination mechanism may produce a polymer with fewer terminal double bonds, whereas a disproportionation mechanism may result in polymers with more terminal functionalities, which may affect the polymer's properties and reactivity. It will be appreciated that controlling termination mechanisms and reaction conditions, such as temperature, monomer concentration, and the presence of impurities or inhibitors, allows for the tailoring of polymer properties for specific applications.

Figure 2A:
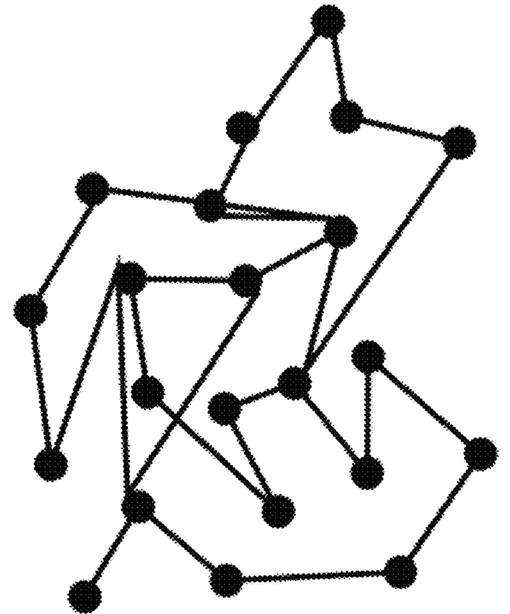
FIGS. 2A-2B schematically illustrate cross-linking mechanisms, comparing a highly crosslinked polymer network (FIG. 2A) and a minimally crosslinked or linear polymer (FIG. 2B) according to one or more embodiments described herein.
Figure 2B:
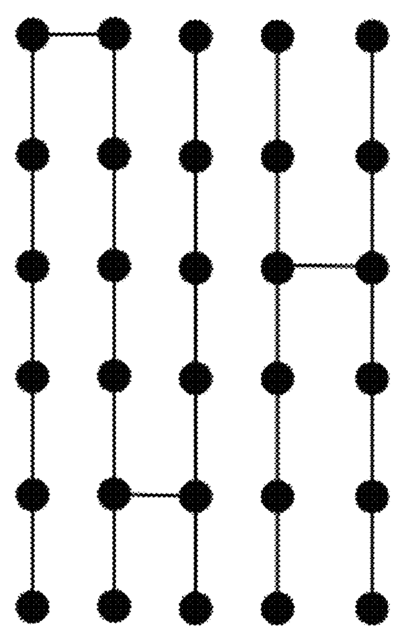

In some embodiments, such as depicted in FIGS. 2A-2B, the polymer in solution exhibits materially less crosslinking (FIG. 2B) compared with bulk polymerization (FIG. 2A). As used herein, "materially less crosslinking" refers to polymerization processes and resultant polymers with a reduced formation of chemical crosslinks between polymer chains compared with bulk polymerization, resulting in more linear polymers. In some embodiments, the amount of crosslinking can be controlled by reducing monomer concentration, slowing reaction rate, increasing chain mobility, and/or swelling of the polymer. In some embodiments, the resultant polymer demonstrates improved ductility and fatigue resistance compared to bulk polymerized acrylic.

Referring again to FIG. 1, in some embodiments, the method 100 involves recovering the acrylic carrier from solution, as depicted at block 110. As used herein, the term "acrylic carrier" refers to the recovered polymer. It will be appreciated that the acrylic carrier may vary based on the polymerization process. In some embodiments, the acrylic carrier is a substantially non-crosslinked, linear or branched polymer.

In some embodiments, the acrylic carrier is a substantially non-crosslinked, linear or branched polymer formed from bulk polymerization with controlled crosslinking. Such embodiments provide acrylic carriers with minimal crosslinking that retain thermoplastic properties.

In some embodiments, the acrylic carrier is a substantially non-crosslinked, linear or branched polymer formed from suspension polymerization, described in greater detail herein. In some embodiments, monomer droplets are dispersed in a continuous aqueous phase and polymerized to form discrete polymer particles. In some embodiments, the resultant acrylic carrier is a substantially non-crosslinked, linear or branched polymer. In some embodiments, suspension polymerization provides a way to create polymers with controlled particle size and distribution.

In some embodiments, the acrylic carrier is a substantially non-crosslinked, linear or branched polymer formed from emulsion polymerization. In some embodiments, emulsion polymerization involves a surfactant to emulsify the monomer in water, creating micelles within which the monomer molecules polymerize. The resulting acrylic carrier is a substantially non-crosslinked, linear or branched polymer with properties that differ from those produced by bulk or suspension polymerization. Emulsion polymerization may result in a polymer with a high molecular weight and a narrow molecular weight distribution, making it suitable for applications requiring high strength and durability.

In some embodiments, the acrylic carrier has materially less crosslinking than that normally resulting from bulk polymerization. By controlling the degree of crosslinking, the mechanical and physical properties of the acrylic carrier may be tailored to specific needs, providing versatility in its application. In some embodiments, controlled crosslinking enable the acrylic carrier to sufficient flexibility and processability while maintaining the desired mechanical properties.

Any suitable means of recovery is contemplated and possible. For example, and not as a limitation, suitable methods of recovery include precipitation, solvent evaporation, steam stripping, anti-solvent addition, dialysis, centrifugation, and the like. In some embodiments, the acrylic carrier is precipitated out of the solution. In some embodiments, after recovery, the acrylic carrier may undergo further purification to remove impurities, unreacted monomers, or additives. In some embodiments, the acrylic carrier is formed as granules or pellets.

In some embodiments, the acrylic carrier is precipitated out of the solution. In some embodiments, a non-solvent or precipitant is added to the reaction mixture. Optionally, the non-solvent causes the polymer to become insoluble and separated from the reaction mixture. It will be appreciated that the components of the reaction mixture influence the choice of non-solvent. For example, and without being bound by theory, in some embodiments, the non-solvent is miscible with the solvent. In some embodiments, the non-solvent does not dissolve the polymer. Exemplary non-solvents include methanol, ethanol, and hexane.

In some embodiments, the non-solvent is mixed with the polymer solution to form a precipitation solution. In some embodiments, the polymer solution is slowly added to the non-solvent. In some embodiments, the non-solvent is slowly added to the polymer solution. Optionally, the precipitation solution is stirred or agitated while mixing.

In some embodiments, the acrylic carrier is separated from the precipitation solution. Any suitable separation technique is contemplated and possible. In some embodiments, the acrylic carrier is separated by filtration, optionally using vacuum filtration. In some embodiments, the acrylic carrier is collected on the filter medium, with the liquid phase passing through. It will be appreciated that the choice of filter medium is dependent on the particle size of the precipitated polymer and the nature of the solvent/non-solvent system.

In some embodiments, the acrylic carrier is washed with a washing solvent after filtration. For example, in some embodiments, the acrylic carrier may still contain residual solvent, monomer, or other impurities, which are removed by washing. Suitable washing solvents are solvents that do not dissolve the polymer. In some embodiments, the washing solvent is the same as the non-solvent. In some embodiments, the acrylic carrier on the filter is washed by pouring the washing solvent over it and allowing the washing solvent to percolate through the filter. In some embodiments, the acrylic carrier undergoes multiple washing steps.

In some embodiments, the acrylic carrier is dried to remove any residual solvent or moisture. Any suitable process for drying is contemplated and possible. Exemplary drying methods include, but are not limited to, air drying, vacuum drying, and thermal drying. It will be appreciated that the choice of drying method may depend on the polymer's thermal stability and/or the boiling point of the residual solvent.

In some embodiment, further purification steps such as reprecipitation or dialysis may be necessary. Reprecipitation generally involves dissolving the polymer in a good solvent and then reprecipitating by adding a non-solvent to remove impurities that were not eliminated in the initial precipitation. Dialysis may be employed for water-soluble polymers or when using aqueous systems to remove small-molecule impurities by diffusion through a semi-permeable membrane.

In some embodiments, the acrylic carrier is combined with an osteoconductive ceramic. Any suitable method for combining the osteoconductive ceramics with the acrylic carrier is contemplated and possible. Suitable methods for mixing and processing the acrylic carrier with osteoconductive ceramics include compounding extrusion, twin-screw extrusion, Banbury mixing, sigma mixers, roll mills, ribbon blenders, fluidized bed mixing, and high-shear mixers. Illustrative examples of osteoconductive ceramics include, but are not limited to, calcium and/or silicate compounds, such as monocalcium phosphate, tricalcium phosphate, hydroxyapatite, silicate, or bioglass.

In some embodiments, incorporating osteoconductive ceramics into an acrylic carrier enhances the mechanical performance of the resulting composite biomaterial or implant. In some embodiments, the osteoconductive ceramics improve one or more characteristics of mechanical performance in the osteoconductive composite implant. Exemplary characteristics of mechanical performance include an increase in one or more of compressive strength, tensile strength, shear strength, flexural strength, fatigue resistance, and/or fracture toughness. (Inventors: do you have ranges of improvement relative to a control and what the control would be)

In some embodiments, the osteoconductive ceramics interact with the long-chain structure of the acrylic carrier to improve mechanical stability through mechanisms such as interfacial bonding and interlocking. In conventional highly cross-linked acrylic polymers, the dense network of cross-links restricts the flexibility and movement of polymer chains, limiting effective interfacial bonding between the polymer and ceramic particles. This rigidity impairs the dispersion of ceramic particles and thus affects the mechanical properties of the composite. Conversely, the more flexible acrylic carriers of the present disclosure enable better interfacial bonding and dispersion of ceramic particles, leading to enhanced mechanical properties.

The presence of ceramic particles may create stress concentrations in a polymer matrix. For example, in highly cross-linked acrylics, which are more rigid and brittle, these stress concentrations often lead to crack initiation and propagation, negatively impacting the mechanical properties of the composite material. In contrast, embodiments of the present disclosure, allow the polymer chains to more effectively distribute the stress around the ceramic particles, improving the toughness and durability of the composite, because the acrylic carriers are more ductile.

Still referring to FIG. 1, in some embodiments, the method 100 involves melting the acrylic carrier, depicted at block 112. Highly cross-linked acrylics are thermosets, meaning they cannot be remelted and reprocessed after initial curing. This limits the ability to mix and distribute ceramic particles within the polymer matrix evenly after initial polymerization. In contrast, the acrylic carriers of the present disclosure are thermoplastics, which can be remelted and reshaped, allowing for more flexibility in processing and improved integration of ceramic particles. It will be appreciated that this property of the acrylic carriers allows for even distribution of ceramic particles within the polymer matrix post-initial polymerization, as described in greater detail herein, which is not readily achievable with thermoset polymers.

Figure 3:
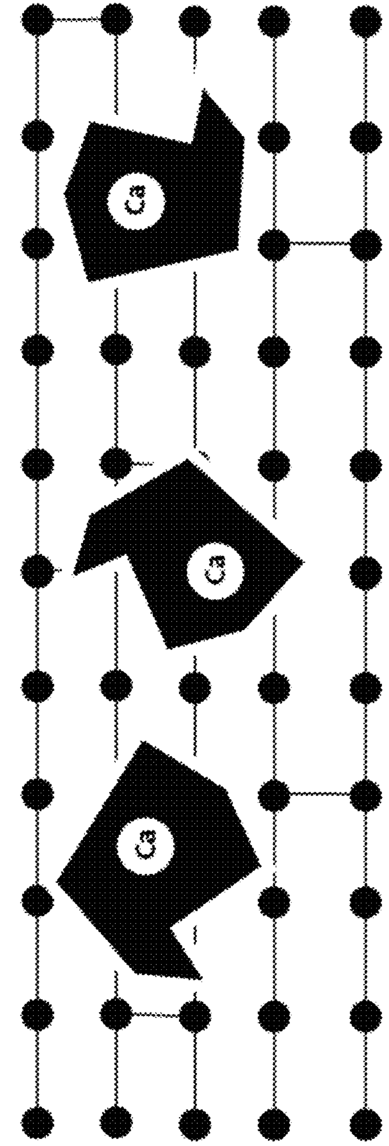
FIG. 3 depicts a diagram showing the interaction between the polymer and ceramic particles at a microscopic level, highlighting the uniform distribution of ceramic within the acrylic matrix, according to one or more embodiments described herein.

In some embodiments, the osteoconductive ceramic granules are mixed with the molten acrylic carrier. In some embodiments, this mixing leads to a dispersion of the ceramic particles throughout the molten acrylic carrier, as illustrated in FIG. 3. In some embodiments, the osteoconductive ceramic is dispersed within the acrylic carrier to provide a mechanically stable network. In some embodiments, the osteoconductive ceramic is uniformly dispersed within the acrylic carrier, thereby enhancing mechanical stability and performance of the implant.

Figure 4:
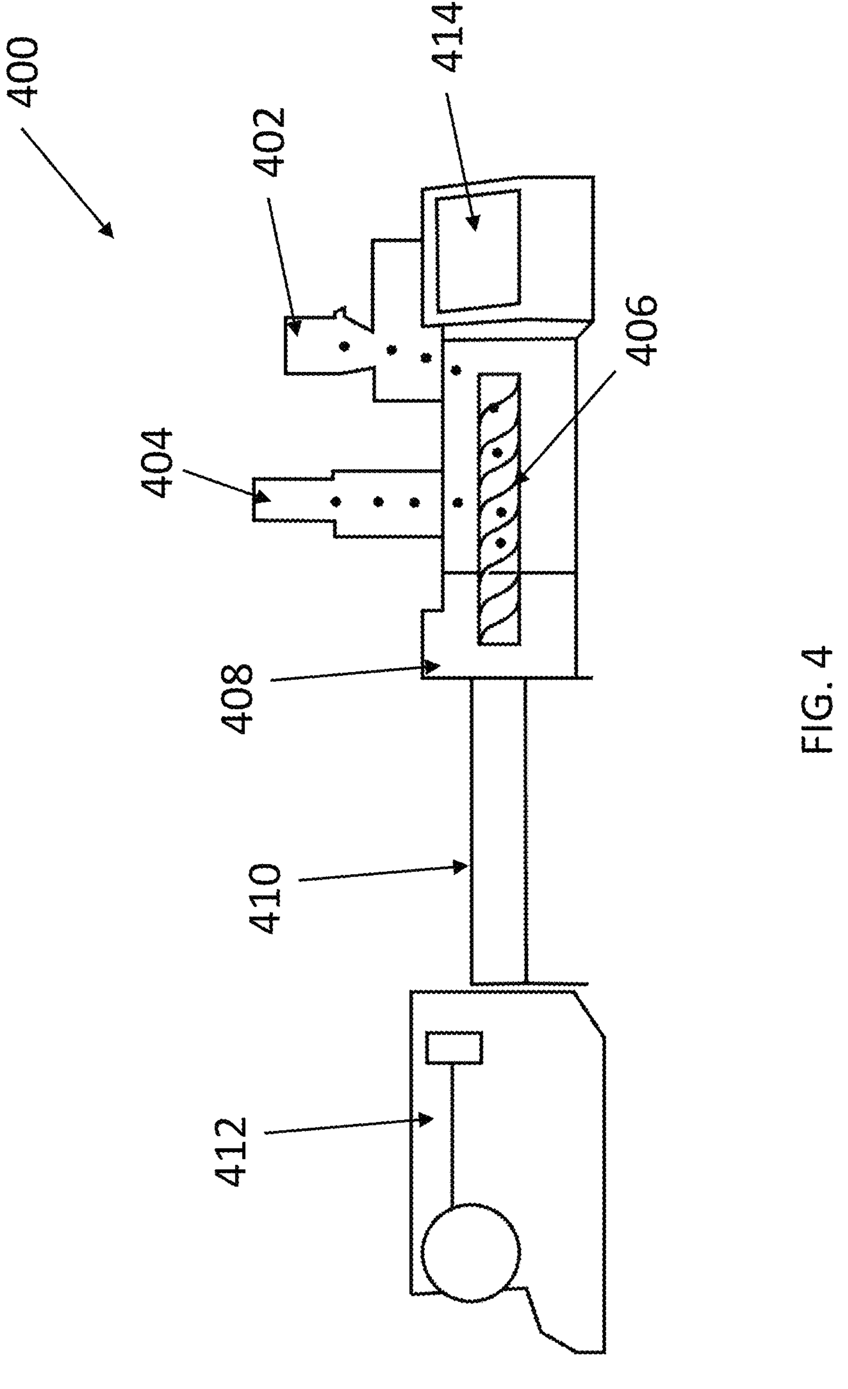
FIG. 4 illustrates a compounding extrusion process for blending the ceramic into the molten acrylic, according to one or more embodiments described herein.

In some embodiments, the method 100 includes mixing the acrylic carrier and the osteoconductive ceramic using compounding extrusion, depicted at block 114 and shown in greater detail in FIG. 4. In some embodiments, the compounding extrusion process results in a uniform dispersion of the ceramic particles in the acrylic carrier. This dispersion within the acrylic carrier provides a mechanically stable network, resulting in improved mechanical performance described in greater detail herein. Compared with traditional methods, the more flexible structure of the acrylic carriers described herein can accommodate a higher volume fraction of ceramic without losing integrity or undergoing phase separation. In some embodiments, the methods described herein allows for a higher ceramic content in the composite material, which enhances the osteoconductive and mechanical properties of the resulting biomaterials and/or implants.

Still referring to FIG. 4, in some embodiments, the dried acrylic carrier is stored in the acrylic hopper 402. The acrylic carrier is fed into the extruder from the acrylic hopper 402. In some embodiments, the osteoconductive ceramic are stored in the ceramic hopper 404. Optionally, the acrylic hopper 402 and/or the ceramic hopper 404 include a volumetric or mass control mechanism 406 to control flow rates of the acrylic carrier and/or the osteoconductive ceramic. In some embodiments, the extrusion process includes adding a controlled mass or volume of the osteoconductive ceramic to the acrylic carrier during the extrusion process. In some embodiments, the controlled mass or volume results in a substantially even dispersal of ceramic within the mixture.

In some embodiments, the compound extruder 400 includes one or more heating elements 408. In some embodiments, the heating elements 408 melt the acrylic carrier, described in greater detail herein. In some embodiments, a screw extruder 406 moves the acrylic carrier and the osteoconductive ceramic granules. In some embodiments, the screw extruder 406 includes a barrel and one or more screws. As the screws rotate within the barrel, the acrylic carrier and the ceramic granules are transported and mixed the materials. Optionally, the mechanical shear generated by the rotating screws may uniformly disperses the ceramic particles within the polymer matrix.

In some embodiments, after the homogenized mixture is extruded, it enters the cooling section 410. In some embodiments, the cooling section 410 section rapidly cools and solidifies the extruded filament. Optionally, the cooling section 410 uses an air or water cooling systems. In some embodiments, cooling the extruded filament maintains the dimensional stability and mechanical properties of the filament.

In some embodiments, the cooled and solidified filament is wound onto spools using a filament spooler 412. In some embodiments, the filament spooler 412 collects the extruded filament in an organized manner. In some embodiments, the filament spooler 412 operates at a controlled speed to match the extrusion rate, preventing any tension or deformation in the filament.

In some embodiments, the entire extrusion process is monitored and controlled by a control system 414. Optionally, the control system 414 system regulates various parameters, including the feed rates of the acrylic powder and ceramic particles, the screw rotation speed, the temperature of the heating elements, and the cooling rate.

In some embodiments, in the compounding extrusion process, acrylic powder from the acrylic hopper 402 and osteoconductive ceramic particles from the ceramic hopper 404 are fed into the screw extruder 406. Optionally, the volumetric control in the ceramic hopper 404 allows for precise proportioning of ceramic particles to achieve the desired composite properties. In some embodiments, as the materials enter the screw extruder 406, the rotating screws convey them forward. In some embodiments, the heating elements 408 melt the acrylic carrier powder, and the ceramic particles are dispersed within the molten polymer through mechanical shear forces generated by the screws. In some embodiments, the homogenized mixture then exits the extruder through a die, forming a continuous filament, or other desired shape of extrusion to form the composite biomaterial, depicted in block 116 of FIG. 1 Optionally, this filament enters the cooling section 410, where it is rapidly cooled and solidified, and is subsequently wound onto spools by the filament spooler 412. In some embodiments, throughout the process, the control system 414 regulates the operational parameters. In some embodiments, the solidified strands are fed into a pelletizer. Optionally, the pelletizer cuts the strands into uniform pellets of the desired size.

Once the osteoconductive composite biomaterial is homogenized and/or solidified, in some embodiments, the resulting mixture is processed into an osteoconductive composite implant, as shown in FIG. 5. For example, in some embodiments, the osteoconductive composite biomaterial is forced through a die at the end of the compounding extruder to shape the material into the desired form. The die may have a specific shape or profile, depending on the intended application.

In some embodiments, the compound extruder 400 is coupled to an injection molding machine. In other embodiments, the pelletized composite biomaterial is fed into an injection molding machine. In some embodiments, the osteoconductive composite biomaterial is injection molded, as depicted at block 116 in FIG. 1. As the composite material is moved through the screw extruder 406, the molten composite may be injected into a mold cavity. Optionally, the injection happens at high pressure, thereby allowing the composite material to flow into all areas of the mold, capturing fine details and complex geometries. In some embodiments, the mold is designed such that the resulting implant will be configured to a subject's anatomical needs, described in greater detail herein.

In some embodiments, the mold is maintained at a lower temperature to facilitate the cooling and solidification of the composite material once it is injected. In some embodiments, during the cooling phase, the material solidifies into the shape of the mold cavity, forming the osteoconductive composite implant. Post-molding surface modifications may be applied to enhance the implant's functionality, ensuring it meets the clinical requirements for successful bone integration and mechanical performance, described in greater detail herein.

In some embodiments, the osteoconductive composite implant is customized to meet the specific needs of a subject. This customization may include tailoring the size, shape, surface characteristics, and/or materials to match the subject's anatomy and/or the clinical requirements of the procedure. For example, the implantation site may be imaged and measured, and the data used to guide the extrusion process through a die, creating a surgical implant that is precisely sized and shaped to meet the subject's individual needs.

Customization of the osteoconductive composite implant may be achieved through various techniques. For example, and without being bound by theory, in some embodiments, patient-specific imaging techniques such as CT scans, MRI, and 3D ultrasound may provide detailed anatomical data from the subject. This data may be used to generate 3D digital models for precise visualization and planning of the implant.

It will be further appreciated that patient-specific surgical planning may employ software for preoperative simulations, to create custom surgical guises, and position the osteoconductive composite implant accurately. In some embodiments, customization of the surgical implant may be adapted based on machine learning algorithms or other artificial intelligence models.

In some embodiments, the osteoconductive implant undergoes surface modification. Exemplary surface modifications include chemical etching, supercritical fluid treatment, mechanical abrasion, and/or plasma spraying to create microscopic features on the surface that promote bone cell attachment and growth. In some embodiments, a solvent may be used to remove a surface layer of acrylic while substantially preserving the embedded ceramic particles to increase surface roughness and external ceramic exposure. Suitable solvents include, but are not limited to, ethanol, methanol, isopropanol, acetone, dimethyl sulfoxide, ethyl acetate, acetonitrile, and/or combinations thereof. In some embodiments, the solvent is isopropyl alcohol.

In some embodiments, the present disclosure relates to a method for producing an osteoconductive composite implant. The method generally involves dissolving a monomer and an initiator in a solvent to form a reaction mixture, controlling the temperature and viscosity of the reaction mixture to allow solution polymerization, polymerizing the monomer in the reaction mixture to form an acrylic carrier, recovering the acrylic carrier, extruding the acrylic carrier with an osteoconductive ceramic to form an osteoconductive biomaterial, and processing the osteoconductive biomaterial to form the osteoconductive composite implant. In some embodiments, the monomer used is methyl methacrylate and the initiator is azobisisobutyronitrile. Optionally, the solvent is absolute ethanol. The reaction mixture may further include a crosslinking copolymer, such as allyl methacrylate. The osteoconductive ceramic may be hydroxyapatite, tricalcium phosphate, calcium phosphate, silicate, or bioglass. In some embodiments, the addition of the osteoconductive ceramic improves the mechanical performance of the osteoconductive composite implant, enhancing characteristics such as compressive strength, tensile strength, shear strength, flexural strength, fatigue resistance, or fracture toughness. In some embodiments, the interaction between the osteoconductive ceramic and the long-chain structure of the solution-polymerized acrylic enhances mechanical stability through interfacial bonding, interlocking, or both. Optionally, the osteoconductive ceramic is dispersed within the acrylic carrier to create a mechanically stable network. In some embodiments, during the extrusion process, a controlled mass or volume of the osteoconductive ceramic is added to the acrylic carrier, resulting in a substantially even dispersal of ceramic within the mixture, which improves the mechanical performance of the osteoconductive composite implant.

In some embodiments, the present disclosure relates to a method for producing an osteoconductive ceramic biomaterial using a substantially non-crosslinked, linear, or branched acrylic carrier. In some embodiments, the method involves dissolving a monomer and an initiator in a solvent to form a reaction mixture. Optionally, the acrylic carrier is produced through one of three polymerization processes: bulk polymerization with controlled crosslinking, suspension polymerization, or emulsion polymerization. In some embodiments, such as in bulk polymerization with controlled crosslinking, the acrylic carrier produced has minimal crosslinking, retaining its thermoplastic properties. In some embodiments, such as in suspension polymerization, the monomer is polymerized in a continuous aqueous phase, forming discrete polymer particles. In some embodiments, such as in emulsion polymerization, the monomer molecules polymerize within formed micelles.

Optionally, once the acrylic carrier is formed, it is subjected to a compounding extrusion process with an osteoconductive ceramic to create an osteoconductive biomaterial. In some embodiments, the osteoconductive biomaterial is processed into an osteoconductive composite implant. Optionally, to enhance the implant's performance, surface modification may be applied, wherein a solvent removes a surface layer of acrylic while preserving the embedded ceramic particles. In some embodiments, this process increases surface roughness and external ceramic exposure, improving the implant's osteoconductive properties.

Aspects Listing:

In a first aspect, alone or in combination with any other aspect disclosed herein, the present disclosure relates to a method for producing an osteoconductive composite implant, the method comprising: dissolving a monomer and an initiator in a solvent to form a reaction mixture; controlling the temperature and viscosity of the reaction mixture to allow solution polymerization; polymerizing the monomer in the reaction mixture to form an acrylic carrier; recovering the acrylic carrier; extruding the acrylic carrier with an osteoconductive ceramic to form an osteoconductive biomaterial; and processing the osteoconductive biomaterial to form the osteoconductive composite implant.

In a second aspect, alone or in combination with any other aspect disclosed herein, the present disclosure relates to a method for producing an osteoconductive composite implant, wherein the monomer is methyl methacrylate.

In a third aspect, alone or in combination with any other aspect disclosed herein, the present disclosure relates to a method for producing an osteoconductive composite implant wherein the initiator is azobisisobutyronitrile (AIBN).

In a fourth aspect, alone or in combination with any other aspect disclosed herein, the present disclosure relates to a method for producing an osteoconductive composite implant wherein the solvent is absolute ethanol.

In a fifth aspect, alone or in combination with any other aspect disclosed herein, the present disclosure relates to a method for producing an osteoconductive composite implant, wherein the reaction mixture further comprises a crosslinking copolymer.

In a sixth aspect, alone or in combination with any other aspect disclosed herein, the present disclosure relates to a method for producing an osteoconductive composite implant, wherein the crosslinking copolymer is allyl methacrylate.

In a seventh aspect, alone or in combination with any other aspect disclosed herein, the present disclosure relates to a method for producing an osteoconductive composite implant, wherein the osteoconductive ceramic is hydroxyapatite, tricalcium phosphate, calcium phosphate, silicate, or bioglass.

In an eighth aspect, alone or in combination with any other aspect disclosed herein, the present disclosure relates to a method for producing an osteoconductive composite implant, wherein the osteoconductive ceramic improves one or more characteristics of mechanical performance in the osteoconductive composite implant.

In a ninth aspect, alone or in combination with any other aspect disclosed herein, the present disclosure relates to a method for producing an osteoconductive composite implant, wherein the one or more characteristics of mechanical performance are selected from an increase in one or more of compressive strength, tensile strength, shear strength, flexural strength, fatigue resistance, or fracture toughness.

In a tenth aspect, alone or in combination with any other aspect disclosed herein, the present disclosure relates to a method for producing an osteoconductive composite implant, wherein the osteoconductive ceramic interacts with the long-chain structure of the solution-polymerized acrylic to enhance mechanical stability.

In an eleventh aspect, alone or in combination with any other aspect disclosed herein, the present disclosure relates to a method for producing an osteoconductive composite implant, wherein the interaction between the osteoconductive ceramic and the long-chain structure of the solution-polymerized acrylic includes interfacial bonding, interlocking, or both.

In a twelfth aspect, alone or in combination with any other aspect disclosed herein, the present disclosure relates to a method for producing an osteoconductive composite implant, wherein the osteoconductive ceramic is dispersed within the acrylic carrier to provide a mechanically stable network.

In a thirteenth aspect, alone or in combination with any other aspect disclosed herein, the present disclosure relates to a method for producing an osteoconductive composite implant, further comprising adding a controlled mass or volume of the osteoconductive ceramic to the acrylic carrier during the extrusion process.

In a fourteenth aspect, alone or in combination with any other aspect disclosed herein, the present disclosure relates to a method for producing an osteoconductive composite implant, wherein the controlled mass or volume of the osteoconductive results in a substantially even dispersal of ceramic within the mixture.

In a fifteenth aspect, alone or in combination with any other aspect disclosed herein, the present disclosure relates to a method for producing an osteoconductive composite implant, wherein the substantially even dispersal of ceramic within the mixture improves the mechanical performance of the osteoconductive composite implant.

In a sixteenth aspect, alone or in combination with any other aspect disclosed herein, the present disclosure relates to a method for producing an osteoconductive ceramic biomaterial, the method comprising: dissolving a monomer and an initiator in a solvent to form a reaction mixture; producing a substantially non-crosslinked or linear acrylic carrier via a process selected from bulk polymerization with controlled crosslinking, suspension polymerization, or emulsion polymerization; subjecting the acrylic carrier to a compounding extrusion process with an osteoconductive ceramic to form an osteoconductive biomaterial; and processing the osteoconductive biomaterial into a osteoconductive composite implant.

In a seventeenth aspect, alone or in combination with any other aspect disclosed herein, the present disclosure relates to a method for producing an osteoconductive ceramic biomaterial, wherein the process is bulk polymerization with controlled crosslinking and wherein the bulk polymerization produces an acrylic carrier with minimal crosslinking that retains thermoplastic properties.

In an eighteenth aspect, alone or in combination with any other aspect disclosed herein, the present disclosure relates to a method for producing an osteoconductive ceramic biomaterial, wherein the process is suspension polymerization and wherein the monomer is polymerized in a continuous aqueous phase to form discrete polymer particles.

In a nineteenth aspect, alone or in combination with any other aspect disclosed herein, the present disclosure relates to a method for producing an osteoconductive ceramic biomaterial, wherein the process is emulsion polymerization and wherein the monomer molecules polymerize within formed micelles.

In a twentieth aspect, alone or in combination with any other aspect disclosed herein, the present disclosure relates to a method for producing an osteoconductive ceramic biomaterial, wherein the osteoconductive composite implant undergoes surface modification with a solvent to remove the surface layer of acrylic but substantially preserve embedded ceramic particles to increase surface roughness and external ceramic exposure.

It is noted that the terms "materially," "substantially," and "about" may be utilized herein to represent the inherent degree of uncertainty that may be attributed to any quantitative comparison, value, measurement, or other representation. These terms are also utilized hercin to represent the degree by which a quantitative representation may vary from a stated reference without resulting in a change in the basic function of the subject matter at issue. The term "materially" and "substantially" are used herein also to represent the degree by which a quantitative representation may vary from a stated reference without resulting in a change in the basic function of the subject matter at issue. Thus, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something less than exact.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" or "including" a second component, it is contemplated that, in some embodiments, the first component "consists" or "consists essentially of" the second component. Additionally, the term "consisting essentially of" is used in this disclosure to refer to quantitative values that do not materially affect the basic and novel characteristic(s) of the disclosure.

It should be understood that any two quantitative values assigned to a property or measurement may constitute a range of that property or measurement, and all combinations of ranges formed from all stated quantitative values of a given property or measurement are contemplated in this disclosure.

While particular embodiments have been illustrated and described herein, it should be understood that various other changes and modifications may be made without departing from scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for producing an osteoconductive composite implant, the method comprising:
- dissolving a monomer and an initiator in a solvent to form a reaction mixture;
- controlling the temperature and viscosity of the reaction mixture to allow solution polymerization;
- polymerizing the monomer in the reaction mixture to form an acrylic carrier;
- recovering the acrylic carrier;
- extruding the acrylic carrier with an osteoconductive ceramic to form an osteoconductive biomaterial; and
- processing the osteoconductive biomaterial to form the osteoconductive composite implant.

2. The method of claim 1, wherein the monomer is methyl methacrylate.

3. The method of claim 1, wherein the initiator is azobisisobutyronitrile (AIBN).

4. The method of claim 1, wherein the solvent is absolute ethanol.

5. The method of claim 1, wherein the reaction mixture further comprises a crosslinking copolymer.

6. The method of claim 5, wherein the crosslinking copolymer is allyl methacrylate.

7. The method of claim 1, wherein the osteoconductive ceramic is hydroxyapatite, tricalcium phosphate, calcium phosphate, silicate, or bioglass.

8. The method of claim 1, wherein the osteoconductive ceramic improves one or more characteristics of mechanical performance in the osteoconductive composite implant.

9. The method of claim 8, wherein the one or more characteristics of mechanical performance are selected from an increase in one or more of compressive strength, tensile strength, shear strength, flexural strength, fatigue resistance, or fracture toughness.

10. The method of claim 1, wherein the osteoconductive ceramic interacts with the long-chain structure of the solution-polymerized acrylic to enhance mechanical stability.

11. The method of claim 10, wherein the interaction between the osteoconductive ceramic and the long-chain structure of the solution-polymerized acrylic includes interfacial bonding, interlocking, or both.

12. The method of claim 1, wherein the osteoconductive ceramic is dispersed within the acrylic carrier to provide a mechanically stable network.

13. The method of claim 1, further comprising adding a controlled mass or volume of the osteoconductive ceramic to the acrylic carrier during the extrusion process.

14. The method of claim 13, wherein the controlled mass or volume of the osteoconductive results in a substantially even dispersal of ceramic within the mixture.

15. The method of claim 14, wherein the substantially even dispersal of ceramic within the mixture improves the mechanical performance of the osteoconductive composite implant.

16. A method for producing an osteoconductive ceramic biomaterial, the method comprising:
- dissolving a monomer and an initiator in a solvent to form a reaction mixture;
- producing a substantially non-crosslinked or linear acrylic carrier via a process selected from bulk polymerization with controlled crosslinking, suspension polymerization, or emulsion polymerization;
- subjecting the acrylic carrier to a compounding extrusion process with an osteoconductive ceramic to form an osteoconductive biomaterial; and
- processing the osteoconductive biomaterial into a osteoconductive composite implant.

17. The method of claim 16, wherein the process is bulk polymerization with controlled crosslinking and wherein the bulk polymerization produces an acrylic carrier with minimal crosslinking that retains thermoplastic properties.

18. The method of claim 16, wherein the process is suspension polymerization and wherein the monomer is polymerized in a continuous aqueous phase to form discrete polymer particles.

19. The method of claim 16, wherein the process is emulsion polymerization and wherein the monomer molecules polymerize within formed micelles.

20. The method of claim 16, wherein the osteoconductive composite implant undergoes surface modification with a solvent to remove the surface layer of acrylic but substantially preserve embedded ceramic particles to increase surface roughness and external ceramic exposure.

* * * * *